US006816572B2

(12) United States Patent
Jabri et al.

(10) Patent No.: US 6,816,572 B2
(45) Date of Patent: Nov. 9, 2004

(54) METHOD, SYSTEM AND COMPUTER PRODUCT FOR PROCESSING DUAL ENERGY IMAGES

(75) Inventors: Kadri Nizar Jabri, Waukesha, WI (US); Gopal B. Avinash, New Berlin, WI (US); Amber Elaine Rader, New Berlin, WI (US); Renuka Uppaluri, Pewaukee, WI (US); John Michael Sabol, Sussex, WI (US); Francois Serge Nicolas, Gif-sur-Yvette (FR)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 120 days.

(21) Appl. No.: 09/683,990

(22) Filed: Mar. 8, 2002

(65) Prior Publication Data

US 2003/0169848 A1 Sep. 11, 2003

(51) Int. Cl.$^7$ ................................................. H05G 1/64
(52) U.S. Cl. ................... 378/98.9; 378/98.8; 378/98.12
(58) Field of Search ............................ 378/98.9, 98.11, 378/98.12, 56, 55, 57, 5, 4, 16, 62, 9, 98.8, 901; 382/132, 128; 600/427

(56) References Cited

U.S. PATENT DOCUMENTS

| | | | |
|---|---|---|---|
| 5,020,085 A | * | 5/1991 | Kawara et al. .......... 378/98.11 |
| 5,396,530 A | | 3/1995 | Tsutsui et al. |
| 6,320,931 B1 | | 11/2001 | Arnold |
| 6,343,111 B1 | | 1/2002 | Avinash et al. |
| 6,570,955 B1 | * | 5/2003 | Siffert et al. ................... 378/54 |
| 6,580,779 B2 | * | 6/2003 | Avinash et al. ............ 378/98.9 |
| 6,614,874 B2 | | 9/2003 | Avinash |
| 6,661,873 B2 | * | 12/2003 | Jabri et al. ................ 378/98.11 |
| 6,683,934 B1 | * | 1/2004 | Zhao et al. ..................... 378/9 |
| 2001/0048732 A1 | | 12/2001 | Wilson et al. |
| 2002/0087074 A1 | * | 7/2002 | Nicolas et al. .............. 600/427 |
| 2003/0095715 A1 | | 5/2003 | Avinash |
| 2003/0142787 A1 | | 7/2003 | Jabri et al. |

* cited by examiner

Primary Examiner—Edward J. Glick
Assistant Examiner—Irakli Kiknadze
(74) Attorney, Agent, or Firm—Cantor Colburn LLP

(57) ABSTRACT

A method of processing dual energy images. The method includes obtaining a first image generated at a first energy level and obtaining a second image generated at a second energy level different than the first energy level. The first and second images are pre-processed and decomposed to form a raw soft-tissue image and a raw bone image. The raw soft-tissue image is post-processed to form a processed soft-tissue image and the raw bone image is post-processed to form a processed bone image. The processed soft-tissue image and the processed bone image are then display processed.

21 Claims, 4 Drawing Sheets

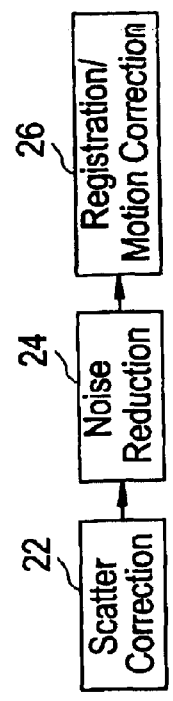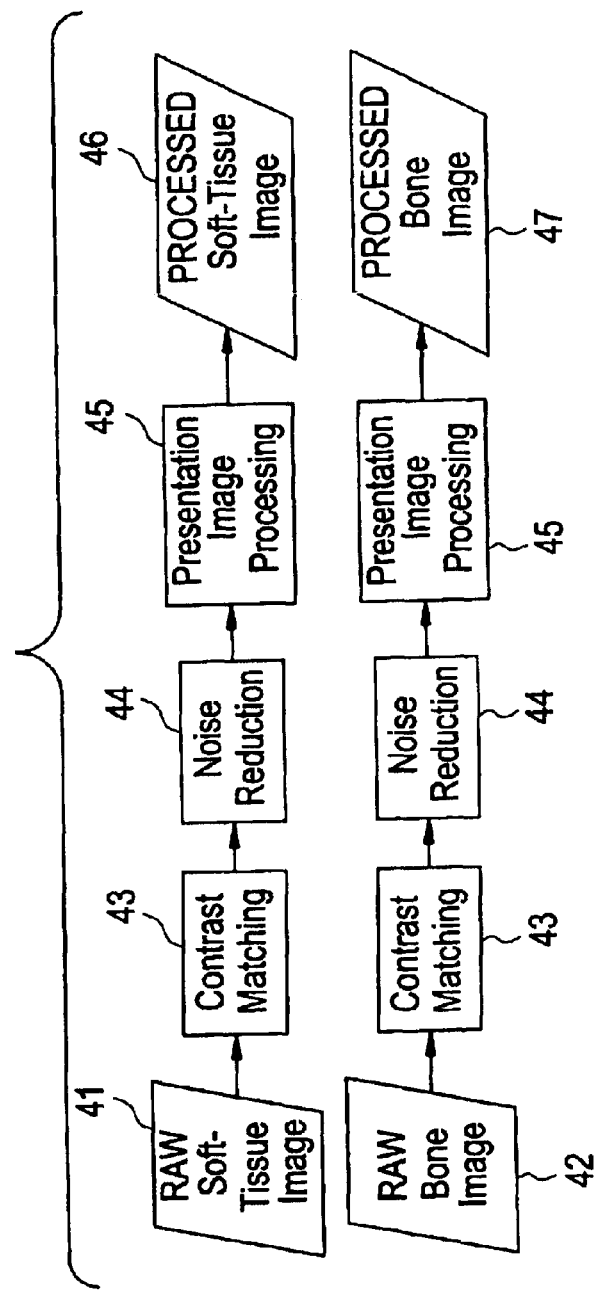

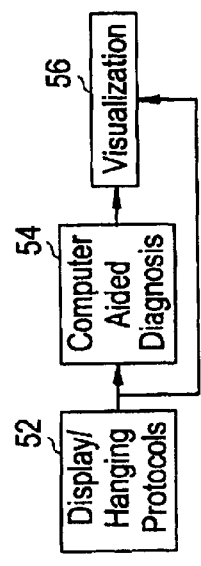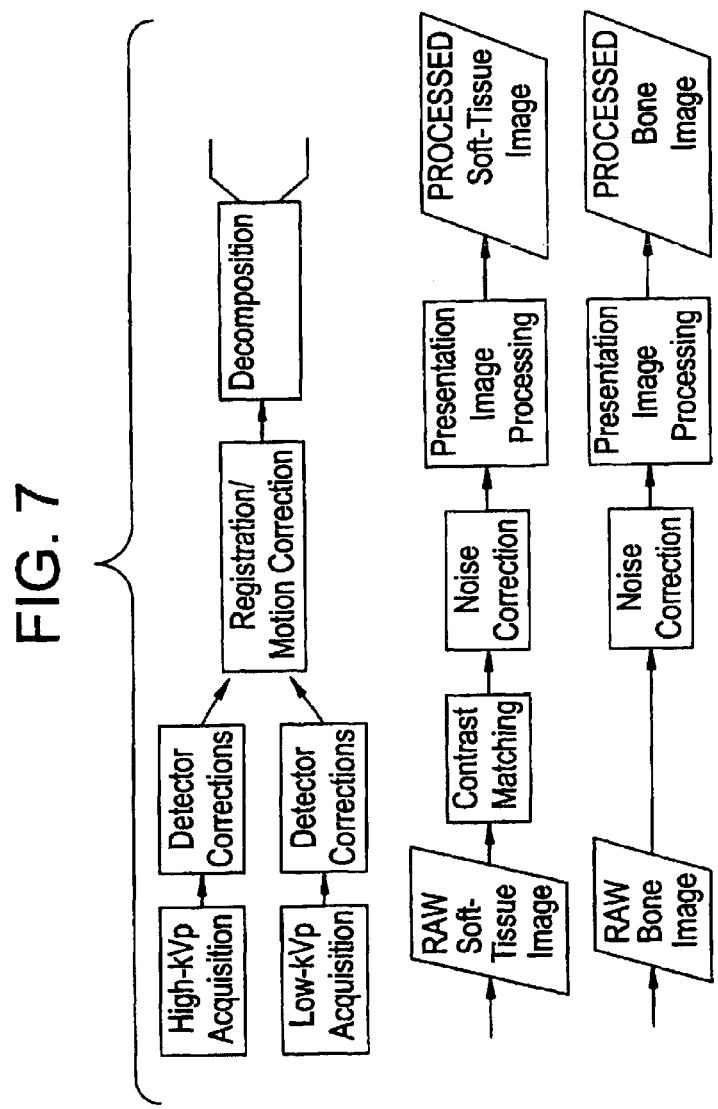
FIG. 6
FIG. 7

METHOD, SYSTEM AND COMPUTER PRODUCT FOR PROCESSING DUAL ENERGY IMAGES

BACKGROUND OF INVENTION

The present disclosure relates generally to dual energy imaging and in particular, to a method and system for processing dual energy images.

Dual energy (DE) radiography involves the acquisition of two x-ray images at different energies within a small time interval. The two images are then used to decompose the imaged anatomy and create soft-tissue and bone images. Existing digital radiography (DR) image acquisition and processing techniques were not designed for DE radiography. Several problems arise when utilizing existing DR image acquisition and processing techniques with DE radiography images. Such problems include residual bone structures in soft-tissue images and residual soft-tissue structures in bone images due to patient motion in-between exposures. In addition, lung/heart motion artifacts due to heart/aortic pulsatile motion may be present. Decomposition artifacts due to significant x-ray scatter may be present and increased noise due to the DE decomposition processing may be experienced. The contrast in the soft-tissue image may not match that in standard images, making the soft-tissue image look "unconventional" to experienced viewers of radiography images.

SUMMARY OF INVENTION

One aspect of the invention is a method of processing dual energy images. The method includes obtaining a first image generated at a first energy level and obtaining a second image generated at a second energy level different than the first energy level. The first and second images are pre-processed and decomposed to form a raw soft-tissue image and a raw bone image. The raw soft-tissue image is post-processed to form a processed soft-tissue image and the raw bone image is post-processed to form a processed bone image. The processed soft-tissue image and the processed bone image are then display processed.

Another aspect of the invention is a method of examining a structure including exposing the structure to an energy source at a first energy level and acquiring a first image of the structure. The structure is exposed to an energy source at a second energy level different than the first energy level and a second image of the structure is acquired. The first image and the second image are pre-processed and then decomposed to form a raw soft-tissue image and a raw bone image. The raw soft-tissue image is post-processed to form a processed soft-tissue image and the raw bone image is processed to form a processed bone image. The processed soft-tissue image and the processed bone image are then display processed.

Another aspect of the invention is a dual energy imaging system including an energy source generating photons at a first energy level and a second energy level different than the first energy level. A detector generates a first image representative of the photons at the first energy level passing through a structure and a second image representative of the photons at the second energy level passing through the structure. A memory coupled to the detector stores the first image and the second image. A processing circuit coupled to the memory pre-processes and post-processes the first and second image. A display device coupled to the processor displays one of the processed first image and the processed second image.

Another aspect of the invention is a dual energy imaging system including an energy means for generating photons at a first energy level and a second energy level different than the first energy level. A detection means generates a first image representative of the photons at the first energy level passing through a structure and a second image representative of the photons at the second energy level passing through the structure. A storage means stores the first image and the second image. A processing means pre-processes the first image and said second image and decomposes the first image and the second image to form a raw soft-tissue image and a raw bone image. The raw soft-tissue image is post-processed to form a processed soft-tissue image and the raw bone image is post-processed to form a processed bone image. A display means displays one of the processed soft-tissue image and the processed bone image.

Another aspect of the invention is a computer program product for processing dual energy images. The computer program product includes a storage medium readable by a processing circuit and storing instructions for execution by the processing circuit. In response to the instructions, the processing circuit obtains a first image generated at a first energy and a second image generated at a second energy different than the first energy level. The processing circuit pre-processes the first image and the second image and decomposes the first image and the second image to form a raw soft-tissue image and a raw bone image. The processing circuit post-processes the raw soft-tissue image to form a processed soft-tissue image. The processing circuit post-processes the raw bone image to form a processed bone image. The processing circuit display processes the processed soft-tissue image and the processed bone image.

BRIEF DESCRIPTION OF DRAWINGS

Referring to the exemplary drawings wherein like elements are numbered alike in the several Figures:

FIG. 4 is a flowchart of exemplary image pre-processing;

FIG. 5 is a flowchart of exemplary image post-processing;

FIG. 6 is a flowchart of exemplary image display processing; and,

FIG. 7 is a flowchart of an exemplary image processing method in an embodiment of the invention.

DETAILED DESCRIPTION

Figure 1:
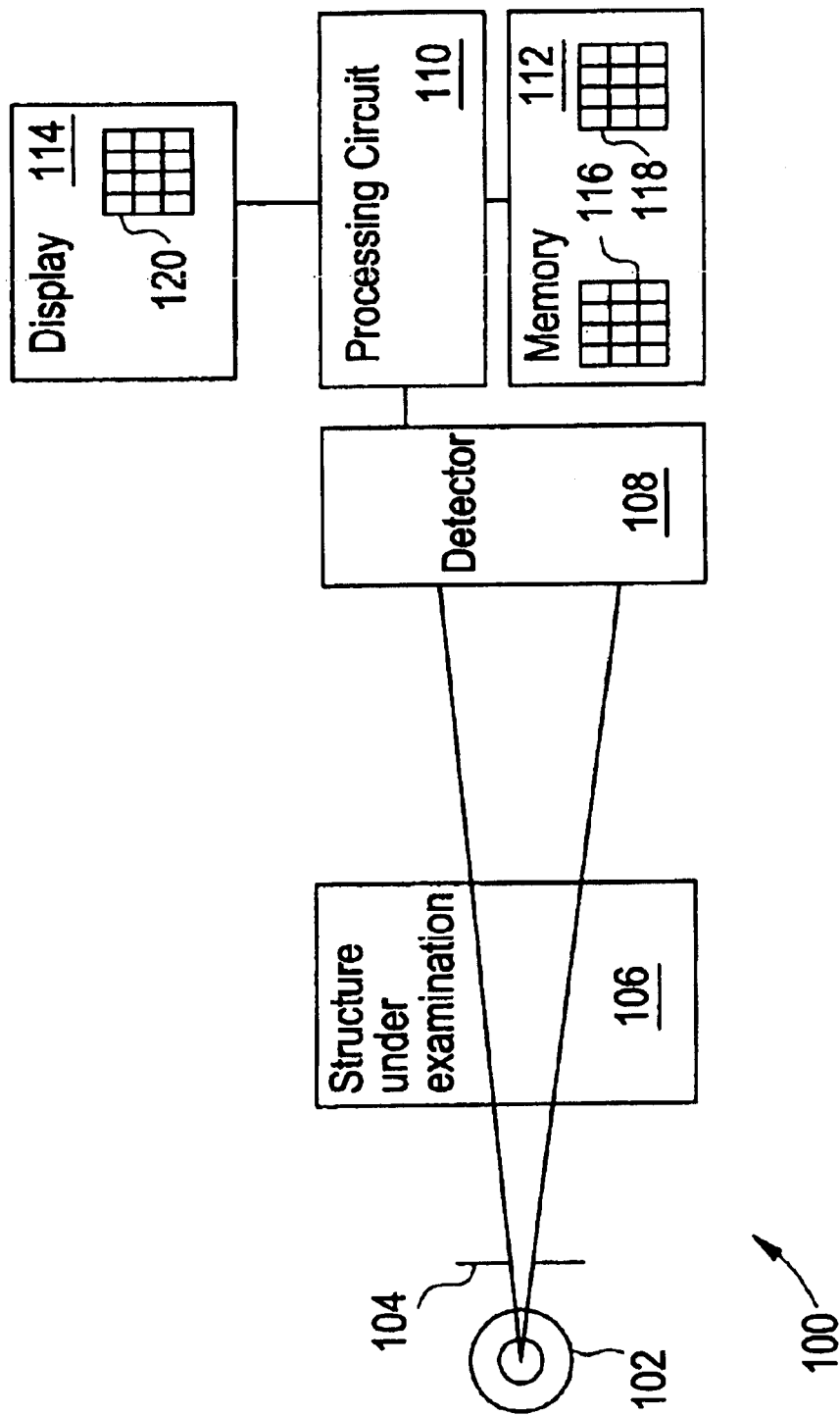
FIG. 1 is a block diagram of an exemplary X-ray imaging system.

FIG. 1 illustrates an exemplary X-ray imaging system 100. The imaging system 100 includes an X-ray source 102 and a collimator 104, which subject structure under examination 106 to X-ray photons. As examples, the X-ray source 102 may be an X-ray tube, and the structure under examination 106 may be a human patient, test phantom or other inanimate object under test.

The X-ray imaging system 100 also includes a detector 108 coupled to a processing circuit 110. The processing circuit 110 (e.g., a microcontroller, microprocessor, custom ASIC, or the like) is coupled to a memory 112 and a display device 114. The memory 112 (e.g., including one or more of a hard disk, floppy disk, CDROM, EPROM, and the like) stores a high energy level image 116 (e.g., an image read out from the detector 108 after 110–140 kVp 5 mAs exposure)

and a low energy level image 118 (e.g., an image read out after 70 kVp 25 mAs exposure). Memory 112 may also store a computer program including instructions executed by the processing circuit 110 to implement the functions described herein. Processing circuit 110 provides an image 120 for display on device 114. As described in further detail herein, the image 120 may representative of different structures (e.g., soft-tissue, bone). The detector 108 may be a flat panel solid state image detector, for example, although conventional film images stored in digital form in the memory 112 may also be processed.

Figure 2:
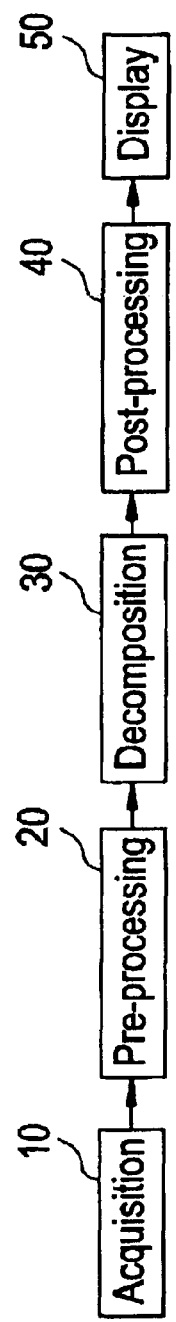
FIG. 2 is a high-level flowchart of an exemplary image acquisition and processing process.
Figure 3:
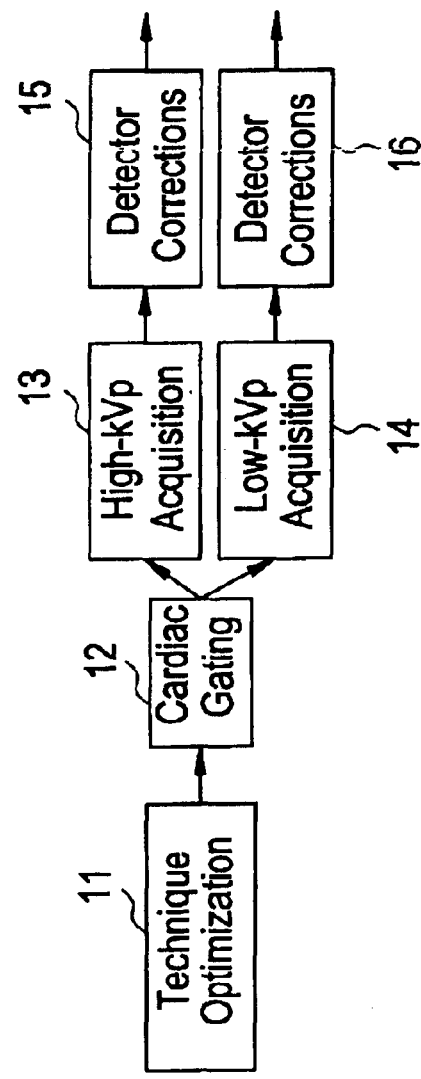
FIG. 3 is a flowchart of exemplary image acquisition processing.

Operation of the system of FIG. 1 will now be described with reference to FIGS. 2–6. FIG. 2 depicts a high-level flowchart of exemplary processing performed by the system of FIG. 1. The process begins at step 10 with image acquisition. An exemplary image acquisition routine is shown in FIG. 3. As shown in FIG. 3, the image acquisition routine includes a technique optimization step 11 that includes processing such as automatic selection of acquisition parameters such as kVp (High and Low), mAs, copper filtration, timing, etc. The acquisition parameters can be based on variables provided by the user (such as patient size) or obtained automatically by the system (such as variables determined by a low-dose "pre-shot"). Selection of the acquisition parameters may address problems such as residual structures, lung/heart motion, decomposition artifacts and contrast.

Once the acquisition parameters are defined, cardiac gating is utilized at step 12. Cardiac gating is a technique that triggers the acquisition of images by detector 108 at a specific point in the cardiac cycle. This reduces heart-motion artifacts in views that include the heart, as well as artifacts indirectly related to heart motion such as lung motion. Cardiac gating addresses lung/heart motion artifacts due to heart/aortic pulsatile motion.

The acquisition of two successive x-ray images at high kVp and low kVp, with a minimum time in between, is depicted as steps 13 and 14, respectively. The filtration of collimator 104 may be changed in between acquisitions to allow for greater separation in x-ray energies. Detector corrections may be applied to both the high energy image and low energy image at steps 15 and 16, respectively. Such detector corrections are known in systems employing flat panel detectors and include techniques such as bad pixel/line correction, gain map correction, etc., as well as corrections specific to dual energy imaging such as laggy pixel corrections.

Referring to FIG. 2, once the acquisition step 10 is completed, flow proceeds to step 20 where the acquired images are pre-processed. FIG. 4 is flowchart of an exemplary pre-processing routine. The pre-processing includes a scatter correction step 22 which may be implemented in software and/or hardware. The scatter correction routine may be applied to each image individually or utilize common information from both the high kVp and the low kVp images to reduce scatter. Existing scatter correction techniques may be used such as hardware solutions including specialized anti-scatter grids, and or software solutions using convolution-based or deconvolution-based methods. Additionally, software techniques can utilize information from one image to tune parameters for the other image. Scatter correction addresses decomposition artifacts due to x-ray scatter.

Once scatter correction is performed, noise reduction is performed at step 24 where one or more existing noise reduction algorithms are applied to the high kVp and the low kVp images, either individually or simultaneously. The noise correction addresses increased noise that may result from the DE decomposition. At step 26, registration is performed to reduce motion artifacts by correcting for motion and aligning anatomies between the high kVp and the low kVp images. The registration algorithms may be known rigid-body or warping registration routines applied to the high kVp and the low kVp images. Alternatively, the techniques may be iterative and make use of the additional information in decomposed soft-tissue and bone images developed at step 30. The registration processing addresses residual structures in the soft-tissue image and/or the bone image and lung/heart motion artifacts.

Referring to FIG. 2, once the pre-processing step 20 is completed, flow proceeds to step 30 where the acquired images are decomposed to generate a raw soft-tissue image and a raw bone image. A standard image (also referred to as a standard posterior-anterior (PA) image) is also defined based on the high kVp image. The decomposition may be performed using known DE radiography techniques. Such techniques may include log-subtraction or basis material decomposition to create raw soft-tissue and raw bone images from the high-energy and low-energy acquisitions. Information from the raw soft-tissue image and raw bone image may be used in the registration/motion correction step 26. For example, edge information and/or artifact location information can be derived from the decomposed images for use in the registration/motion correction.

Referring to FIG. 2, once the decomposition step 30 is completed, flow proceeds to step 40 where the acquired images are post-processed. FIG. 5 is a flowchart of an exemplary post-processing routine. As shown in FIG. 5, the raw soft-tissue image 41 and the raw bone image 42 are subjected to similar processing. Contrast matching 43 is performed match contrast of structures in raw soft-tissue image 41 and the raw bone image 42 to the corresponding structures in a standard image. For example, contrast of soft-tissue structures in raw soft-tissue image 41 (e.g., chest image) is matched to the contrast in the standard PA image. The contrast matching is performed to facilitate interpretation of the x-ray images.

At 44, one or more noise reduction algorithms may be applied to the soft-tissue image 41 and the bone image 42. Existing noise reduction algorithms may be used. The noise reduction addresses noise due to DE decomposition. At 45, presentation image processing may be performed to the soft-tissue image 41 and the bone image 42. The presentation processing includes processes such as edge enhancement, display window level and window width adjustments for optimal display. The result of the post-processing 40 is depicted as processed soft-tissue image 46 and processed bone image 47.

Referring to FIG. 2, once the post-processing step 40 is completed, flow proceeds to step 50 where the acquired images are processed for display. Display is intended to cover multiple display techniques including display on a monitor or by a printer. As shown in FIG. 6, display processing 50 includes designating display options and hanging protocols at step 52 in response to user input (e.g., radiologists preferences). These display options and hanging protocols may be customized or standardized depending on the limitations of workstation where the images are reviewed, picture archiving and communication systems (PACS), etc. For example, the resolution of the image may be adjusted depending on the display and bandwidth capabilities of the workstation where the images are viewed.

At step 54, computer aided diagnosis (CAD) algorithms may be applied to one or all of the processed soft-tissue image, the processed bone image and the standard image. The CAD algorithms may be tailored to the processed soft-tissue image and processed bone image to improve performance. At step 56, the processed soft-tissue image and/or the processed bone image, along with the results of any CAD algorithms are displayed. For example, three image types (standard, soft-tissue and bone) may be viewed dynamically on a single display, either in a time-loop or by manual stepping. This visualization technique can potentially highlight pathologies that are not readily apparent in side-by-side review of images.

FIG. 7 is a flowchart of an exemplary image acquisition and processing routine. As shown in FIG. 7, not all the above-described processing steps are performed, or performed on each image. For example, the contrast matching is performed on the raw soft-tissue image but not on the raw bone image. Thus, the processing steps utilized and the order of the steps as described above is exemplary and not intended to limit the invention.

Although the preceding embodiments are discussed with respect to medical imaging, it is understood that the image acquisition and processing methodology described herein is not limited to medical applications, but may be utilized in non-medical applications.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method of processing dual energy images comprising:

obtaining a first image generated at a first energy level;

obtaining a second image generated at a second energy level different than the first energy level;

pre-processing said first image and said second image, said preprocessing includes performing detector corrections on first image and the second image;

decomposing said first image and said second image to form a raw soft-tissue image and a raw bone image;

post-processing the raw soft-tissue image to form a processed soft-tissue image, said post-processing the raw soft-tissue image includes performing noise reduction on the raw soft-tissue image;

post-processing the raw bone image to form a processed bone image, said post-processing the raw bone image includes performing noise reduction on the raw bone image;

display processing the processed soft-tissue image and the processed bone image.

2. The method of claim 1 wherein:

said pre-processing includes performing registration on at least one of the first image and the second image to correct motion artifacts.

3. The method of claim 1 wherein:

said post-processing the raw soft-tissue image includes adjusting the contrast of the raw soft-tissue image to match a predetermined contrast.

4. The method of claim 1 wherein:

said post-processing the raw soft-tissue image includes performing presentation processing on the raw soft-tissue image, said presentation processing including edge enhancement.

5. The method of claim 1 wherein:

said post-processing the raw bone image includes adjusting the contrast of the raw bone image to match a predetermined contrast.

6. The method of claim 1 wherein:

said post-processing the raw bone image includes performing presentation processing on the raw bone image, said presentation processing including edge enhancement.

7. The method of claim 1 wherein:

said display processing includes displaying at least one of the processed soft-tissue image, the processed raw bone image and a standard image derived from the first image.

8. The method of claim 7 wherein:

said display processing includes displaying the processed soft-tissue image, the processed raw bone image and the standard image in a timed sequence.

9. The method of claim 1 wherein:

said display processing includes performing computer aided diagnosis on at least one of said processed soft-tissue image and said processed bone image and displaying results of said computer aided diagnosis.

10. The method of claim 1 wherein:

said display processing includes designating display options for at least one of the processed soft-tissue image and the processed bone image.

11. A method of examining a structure comprising:

exposing the structure to an energy source at a first energy level;

acquiring a first image of the structure;

exposing the structure to an energy source at a second energy level different than the first energy level;

acquiring a second image of the structure;

pre-processing said first image and said second image, said preprocessing includes performing detector corrections on first image and the second image;

decomposing said first image and said second image to form a raw soft-tissue image and a raw bone image;

post-processing the raw soft-tissue image to form a processed soft-tissue image, said post-processing the raw soft-tissue image includes performing noise reduction on the raw soft-tissue image;

post-processing the raw bone image to form a processed bone image, said post-processing the raw bone image includes performing noise reduction on the raw bone image;

display processing the processed soft-tissue image and the processed bone image.

12. The method of claim 11 wherein:

the structure is a portion of a human;

said acquiring the first image including using cardiac gating to acquire the first image at a specific point in a cardiac cycle.

13. The method of claim 11 wherein:

said acquiring the first image includes adjusting the first image in response to a detector correction.

14. The method of claim 11 wherein:

the structure is a portion of a human;

said acquiring the second image including using cardiac gating to acquire the second image at a specific point in a cardiac cycle.

15. The method of claim 11 wherein:

said acquiring the second image includes adjusting the second image in response to a detector correction.

16. The method of claim 11 wherein:

said display processing includes performing computer aided diagnosis on at least one of said processed soft-tissue image and said processed bone image and displaying results of said computer aided diagnosis.

17. The method of claim 11 wherein:

said display processing includes designating display options for at least one of the processed soft-tissue image and the processed bone image.

18. The method of claim 11 wherein:

said display processing includes displaying the processed soft-tissue image, the processed raw bone image and a standard image derived from the first image in a timed sequence.

19. A dual energy imaging system comprising:

an energy source generating photons at a first energy level and a second energy level different than the first energy level;

a detector generating a first image representative of the photons at the first energy level passing through a structure and a second image representative of the photons at the second energy level passing through the structure;

a memory coupled to the detector, said memory storing the first image and the second image;

a processing circuit coupled to said memory, said processing circuit pre-processing said first image and said second image, said preprocessing includes performing detector corrections on first image and the second image;

post-processing the first image to form a processed first image, said post-processing the first image includes performing noise reduction on the first image;

post-processing the second image to form a processed second image, said post-processing the second image includes performing noise reduction on the second image;

a display device coupled to said processing circuit, said display device displaying one of the processed first image and the processed second image.

20. A dual energy imaging system comprising:

energy means for generating photons at a first energy level and a second energy level different than the first energy level;

detection means for generating a first image representative of the photons at the first energy level passing through a structure and a second image representative of the photons at the second energy level passing through the structure;

storage means for storing the first image and the second image;

processing means for:

pre-processing said first image and said second image, said preprocessing includes performing detector corrections on first image and the second image;

decomposing said first image and said second image to form a raw soft-tissue image and a raw bone image;

post-processing the raw soft-tissue image to form a processed soft-tissue image, said post-processing the raw soft-tissue image includes performing noise reduction on the raw soft-tissue image;

post-processing the raw bone image to form a processed bone image, said post-processing the raw bone image includes performing noise reduction on the raw bone image;

display means for displaying one of the processed soft-tissue image and the processed bone image.

21. A computer program product for processing dual energy images, the product comprising:

a storage medium readable by a processing circuit and storing instructions for execution by the processing circuit for:

obtaining a first image generated at a first energy;

obtaining a second image generated at a second energy different than the first energy level;

pre-processing said first image and said second image, said preprocessing includes performing detector corrections on first image and the second image;

decomposing said first image and said second image to form a raw soft-tissue image and a raw bone image;

post-processing the raw soft-tissue image to form a processed soft-tissue image said post-processing the raw soft-tissue image includes performing noise reduction on the raw soft-tissue image;

post-processing the raw bone image to form a processed bone image, said post-processing the raw bone image includes performing noise reduction on the raw bone image;

display processing the processed soft-tissue image and the processed bone image.

* * * * *